(12) United States Patent
Goldberg

(10) Patent No.: US 9,256,910 B2
(45) Date of Patent: *Feb. 9, 2016

(54) MEDICAL MONITORING/CONSUMABLES TRACKING DEVICE

(75) Inventor: Jason Goldberg, Ontario (CA)

(73) Assignee: Ideal Life, Inc., Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/238,151

(22) Filed: Sep. 21, 2011

(65) Prior Publication Data

US 2012/0010902 A1    Jan. 12, 2012

Related U.S. Application Data

(63) Continuation of application No. 10/963,205, filed on Oct. 11, 2004, now Pat. No. 8,034,294, which is a continuation of application No. 10/892,520, filed on Jul. 15, 2004, now abandoned.

(60) Provisional application No. 60/487,471, filed on Jul. 15, 2003.

(51) Int. Cl.
*G01N 33/00* (2006.01)
*G06Q 50/22* (2012.01)
*G01N 33/487* (2006.01)

(52) U.S. Cl.
CPC .......... *G06Q 50/22* (2013.01); *G01N 33/48792* (2013.01)

(58) Field of Classification Search
CPC ................................. G01N 33/48792
See application file for complete search history.

(56) References Cited

U.S. PATENT DOCUMENTS

| | | | |
|---|---|---|---|
| 3,804,524 A | 4/1974 | Jocoy et al. |
| 4,394,773 A | 7/1983 | Ruell |
| 4,408,323 A | 10/1983 | Montgomery |
| 4,453,247 A | 6/1984 | Suzuki et al. |
| 4,581,735 A | 4/1986 | Flamm et al. |

(Continued)

FOREIGN PATENT DOCUMENTS

| WO | WO 01/65810 | 9/2001 |
|---|---|---|
| WO | WO 01/97703 | 12/2001 |
| WO | WO 03/082091 | * 10/2003 |

OTHER PUBLICATIONS

Ideal Life Pod (Model ILP 0001), Ideal Life Inc., K080535, Jul. 3, 2008, 16 pgs.

(Continued)

*Primary Examiner* — Sam P Siefke
(74) *Attorney, Agent, or Firm* — Jon E. Gordon; Frommer Lawrence & Huag LLP

(57) ABSTRACT

The present invention generally provides medical monitoring devices, and corresponding systems, that includes at least one sensor for detecting usage of at least one consumable, an electronic controller electrically connected to the sensor to receive a signal therefrom produced when consumable usage is detected, and an electronic memory electrically connected to the controller for storing consumable usage data thereon. The medical monitoring device may further include at least one sensor for determining one or more physiological parameter of a subject and a display device for displaying the physiological parameter. The medical monitoring device may also include a communications unit for communicating stored data, such as usage and physiological parameter data, over a communication network to a remote computer.

6 Claims, 3 Drawing Sheets

(56) References Cited

U.S. PATENT DOCUMENTS

| | | | |
|---|---|---|---|
| 4,731,726 A | 3/1988 | Allen, III | |
| 4,782,485 A | 11/1988 | Gollub | |
| 4,831,242 A | 5/1989 | Englehardt et al. | |
| 4,857,916 A | 8/1989 | Bellin | |
| 4,905,293 A | 2/1990 | Asai et al. | |
| 4,914,650 A | 4/1990 | Sriram | |
| 5,077,010 A * | 12/1991 | Ishizaka et al. | 422/408 |
| 5,144,680 A | 9/1992 | Kobayashi et al. | |
| 5,213,555 A | 5/1993 | Hood et al. | |
| 5,307,263 A | 4/1994 | Brown | |
| 5,390,238 A | 2/1995 | Kirk et al. | |
| 5,412,463 A | 5/1995 | Sibbald et al. | |
| 5,420,936 A | 5/1995 | Fitzpatrick et al. | |
| 5,467,403 A | 11/1995 | Fishbine et al. | |
| 5,546,471 A | 8/1996 | Merjanian | |
| 5,576,952 A | 11/1996 | Stutman et al. | |
| 5,590,632 A | 1/1997 | Kato et al. | |
| 5,603,179 A | 2/1997 | Adams | |
| 5,617,423 A | 4/1997 | Li et al. | |
| 5,687,732 A | 11/1997 | Inagaki et al. | |
| 5,701,904 A | 12/1997 | Simmons et al. | |
| 5,704,366 A | 1/1998 | Tacklind et al. | |
| 5,713,350 A | 2/1998 | Yokota et al. | |
| 5,732,133 A | 3/1998 | Mark | |
| 5,772,586 A | 6/1998 | Heionen et al. | |
| 5,796,858 A | 8/1998 | Zhou et al. | |
| 5,822,715 A | 10/1998 | Worthington et al. | |
| 5,827,180 A | 10/1998 | Goodman | |
| 5,828,773 A | 10/1998 | Setlak et al. | |
| 5,828,943 A | 10/1998 | Brown | |
| 5,832,448 A | 11/1998 | Brown | |
| 5,838,306 A | 11/1998 | O'Connor et al. | |
| 5,840,020 A | 11/1998 | Heinonen et al. | |
| 5,852,670 A | 12/1998 | Setlak et al. | |
| 5,862,803 A | 1/1999 | Besson et al. | |
| 5,872,834 A | 2/1999 | Teitelbaum | |
| 5,875,430 A | 2/1999 | Koether | |
| 5,879,163 A | 3/1999 | Brown et al. | |
| 5,897,493 A | 4/1999 | Brown | |
| 5,899,855 A | 5/1999 | Brown | |
| 5,902,234 A | 5/1999 | Webb | |
| 5,910,946 A | 6/1999 | Csapo | |
| 5,920,642 A | 7/1999 | Merjanian | |
| 5,926,261 A | 7/1999 | Hoshino | |
| 5,933,136 A | 8/1999 | Brown | |
| 5,940,801 A | 8/1999 | Brown | |
| 5,950,632 A | 9/1999 | Reber et al. | |
| 5,951,300 A | 9/1999 | Brown | |
| 5,953,322 A | 9/1999 | Kimball | |
| 5,956,501 A | 9/1999 | Brown | |
| 5,957,854 A | 9/1999 | Besson et al. | |
| 5,960,403 A | 9/1999 | Brown | |
| 5,970,458 A | 10/1999 | Petkovset | |
| 5,985,559 A | 11/1999 | Brown | |
| 5,991,408 A | 11/1999 | Pearson et al. | |
| 5,997,476 A | 12/1999 | Brown | |
| 6,011,860 A | 1/2000 | Fujieda et al. | |
| 6,016,476 A | 1/2000 | Maes et al. | |
| 6,024,699 A | 2/2000 | Surwit et al. | |
| 6,028,950 A | 2/2000 | Merjanian | |
| 6,032,119 A | 2/2000 | Brown et al. | |
| 6,047,203 A | 4/2000 | Sackner et al. | |
| 6,050,940 A | 4/2000 | Braun et al. | |
| 6,064,737 A | 5/2000 | Rhoads | |
| 6,072,396 A | 6/2000 | Gaukel | |
| 6,078,848 A | 6/2000 | Bernstein et al. | |
| 6,078,908 A | 6/2000 | Schmitz | |
| 6,088,585 A | 7/2000 | Schmitt et al. | |
| 6,101,478 A | 8/2000 | Brown | |
| 6,111,977 A | 8/2000 | Scott et al. | |
| 6,128,563 A | 10/2000 | Muraro | |
| 6,135,951 A | 10/2000 | Richardson et al. | |
| 6,141,436 A | 10/2000 | Srey et al. | |
| 6,144,837 A | 11/2000 | Quy | |
| 6,151,586 A | 11/2000 | Brown | |
| 6,154,727 A | 11/2000 | Karp et al. | |
| 6,160,903 A | 12/2000 | Hamid et al. | |
| 6,161,095 A | 12/2000 | Brown | |
| 6,167,362 A | 12/2000 | Brown et al. | |
| 6,168,563 B1 | 1/2001 | Brown | |
| 6,175,752 B1 | 1/2001 | Say et al. | |
| 6,175,922 B1 | 1/2001 | Wang | |
| 6,177,950 B1 | 1/2001 | Robb | |
| 6,191,410 B1 | 2/2001 | Johnson | |
| 6,196,970 B1 | 3/2001 | Brown | |
| 6,198,394 B1 | 3/2001 | Jacobson et al. | |
| 6,219,793 B1 | 4/2001 | Li et al. | |
| 6,221,010 B1 | 4/2001 | Lucas | |
| 6,233,539 B1 | 5/2001 | Brown | |
| 6,240,393 B1 | 5/2001 | Brown | |
| 6,246,992 B1 | 6/2001 | Brown | |
| 6,248,065 B1 | 6/2001 | Brown | |
| 6,249,672 B1 | 6/2001 | Castiel | |
| 6,256,737 B1 | 7/2001 | Bianco et al. | |
| 6,260,022 B1 | 7/2001 | Brown | |
| 6,260,065 B1 | 7/2001 | Leiba et al. | |
| 6,270,455 B1 | 8/2001 | Brown | |
| 6,282,304 B1 | 8/2001 | Novikov et al. | |
| 6,289,238 B1 | 9/2001 | Besson et al. | |
| 6,302,844 B1 | 10/2001 | Walker et al. | |
| 6,330,426 B2 | 12/2001 | Brown et al. | |
| 6,330,457 B1 | 12/2001 | Yoon | |
| 6,334,778 B1 | 1/2002 | Brown | |
| 6,337,918 B1 | 1/2002 | Holehan | |
| 6,337,919 B1 | 1/2002 | Dunton | |
| 6,366,871 B1 | 4/2002 | Geva | |
| 6,368,273 B1 | 4/2002 | Brown | |
| 6,375,469 B1 | 4/2002 | Brown | |
| 6,375,614 B1 | 4/2002 | Braun et al. | |
| 6,379,301 B1 | 4/2002 | Worthington et al. | |
| 6,381,577 B1 | 4/2002 | Brown | |
| 6,402,691 B1 | 6/2002 | Peddicord et al. | |
| 6,404,862 B1 | 6/2002 | Holt | |
| 6,440,069 B1 | 8/2002 | Raymond et al. | |
| 6,441,747 B1 | 8/2002 | Khair et al. | |
| 6,454,705 B1 | 9/2002 | Cosentino et al. | |
| 6,478,736 B1 | 11/2002 | Mault | |
| 6,493,437 B1 | 12/2002 | Olshansky | |
| 6,525,670 B1 | 2/2003 | Doi et al. | |
| 6,558,320 B1 | 5/2003 | Causey et al. | |
| 6,577,893 B1 | 6/2003 | Besson et al. | |
| 6,579,231 B1 | 6/2003 | Phipps | |
| 6,589,169 B1 | 7/2003 | Surwit et al. | |
| 6,594,523 B1 | 7/2003 | Levine | |
| 6,595,929 B2 | 7/2003 | Stivoric et al. | |
| 6,599,250 B2 | 7/2003 | Webb et al. | |
| 6,602,191 B2 | 8/2003 | Quy | |
| 6,602,469 B1 * | 8/2003 | Maus et al. | 422/68.1 |
| 6,611,705 B2 | 8/2003 | Hopman et al. | |
| 6,638,218 B2 | 10/2003 | Bulat | |
| 6,643,542 B1 | 11/2003 | Kawanishi | |
| 6,658,287 B1 | 12/2003 | Litt et al. | |
| 6,694,186 B2 | 2/2004 | Bardy | |
| 6,699,195 B2 | 3/2004 | Nakazawa et al. | |
| 6,725,209 B1 | 4/2004 | Iliff | |
| 6,749,537 B1 | 6/2004 | Hickman | |
| 6,770,029 B2 | 8/2004 | Iliff | |
| 6,840,904 B2 | 1/2005 | Goldberg | |
| 7,024,369 B1 | 4/2006 | Brown et al. | |
| 7,261,690 B2 | 8/2007 | Teller et al. | |
| 7,448,996 B2 | 11/2008 | Khanuja et al. | |
| 2001/0012201 A1 | 8/2001 | Fries et al. | |
| 2001/0048025 A1 | 12/2001 | Shinn | |
| 2001/0048359 A1 | 12/2001 | Yamane et al. | |
| 2001/0049785 A1 | 12/2001 | Kawan et al. | |
| 2001/0051924 A1 | 12/2001 | Uberti | |
| 2002/0003892 A1 | 1/2002 | Iwanaga | |
| 2002/0010857 A1 | 1/2002 | Karthik | |
| 2002/0016719 A1 | 2/2002 | Nemeth et al. | |
| 2002/0022973 A1 | 2/2002 | Sun et al. | |
| 2002/0065682 A1 | 5/2002 | Goldenberg | |
| 2002/0106077 A1 | 8/2002 | Moquin et al. | |
| 2002/0120200 A1 | 8/2002 | Brockway et al. | |
| 2002/0122415 A1 | 9/2002 | Chang et al. | |

(56) References Cited

U.S. PATENT DOCUMENTS

| | | |
|---|---|---|
| 2002/0128804 A1 | 9/2002 | Geva |
| 2002/0133377 A1 | 9/2002 | Brown |
| 2002/0152391 A1 | 10/2002 | Willins et al. |
| 2002/0174345 A1 | 11/2002 | Patel |
| 2003/0046557 A1 | 3/2003 | Miller et al. |
| 2003/0081752 A1 | 5/2003 | Trandal |
| 2003/0126593 A1 | 7/2003 | Mault |
| 2004/0019259 A1 | 1/2004 | Brown et al. |
| 2004/0034286 A1 | 2/2004 | Kasper et al. |
| 2004/0059599 A1 | 3/2004 | McIvor |
| 2004/0102683 A1 | 5/2004 | Khanuja et al. |
| 2004/0152957 A1 | 8/2004 | Stivoric et al. |
| 2004/0152993 A1 | 8/2004 | Bardy |
| 2004/0167580 A1 | 8/2004 | Mann et al. |
| 2004/0230127 A1 | 11/2004 | Bardy |
| 2005/0137481 A1 | 6/2005 | Sheard et al. |
| 2005/0144042 A1 | 6/2005 | Joffe et al. |
| 2005/0203349 A1 | 9/2005 | Nanikashvili |

OTHER PUBLICATIONS

OMRON Automatic Blood Pressure Monitor With Intellisense, Models HEM-773, HEM-773AC, OMRON Healthcare, Inc., K021682, 4 pgs.

Our Solutions, Carematix WellnessSystem, © 2002, 1 pg.

Update to IN TOUCH® Diabetes Mangement Software, LIFESCAN, © 2001, 1 pg.

Hardesty, Larry, "Clothed in Health," Technology Review, Jul./Aug. 2001, p. 34.

"Micropaq," Welch Allyn, http://www.monitoring.welchallyn.com/products/wireless/micropaq.asp, retrieved Apr. 16, 2003, 2 pgs.

Home Health Telemanagement Service, The University of Illinois at Chicago Medical Center, http://www.uic.edu/hsc/acad/intmed/cardio/monitor/, retrieved Jul. 13, 2005, 1 pg.

Boston medical, http://www.bosmedtech.com, retrieved Oct. 10, 2001, 2 pgs.

Kivalo: Wireless Healthcare Informatics, http://www.kivalo.com/, retrieved Oct. 10, 2001, 2 pgs.

"Digital Angel: Making Your World a Little Safer . . . ," http://www.digitalangel.net/da/, retrieved Oct. 10, 2001, 7 pgs.

Cardionet, http://www.cardionet.com/, retrieved Oct. 10, 2001, 1 pg.

The HomMed Central Station, http://www.hommed.com/patients_families/central_station.asp, retrieved Oct. 10, 2001, 1 pg.

"BodyMedia Introduces SenseWear Pro Armband Wireless Body Monitoring Device," http://www.thinkmobile.com/news/00/39/23/, retrieved Oct. 10, 2001, 3 pgs.

U.S. Appl. No. 10/081,132, Goldberg.

U.S. Appl. No. 10/868,676, Goldberg.

U.S. Appl. No. 10/913,140, Goldberg.

U.S. Appl. No. 11/108,355, Goldberg.

U.S. Appl. No. 11/356,739, Goldberg.

U.S. Appl. No. 12/509,119, Goldberg.

Hardesty, Larry, "Clothes in Health," Technology Review. Jul./Aug. 2001, p. 34.

Home Health Telemanagement Service, The University of Illinois at Chicago Medical Center, http://www.uic.edu/hse/acad/intmed/cardio/monitor retrieved Jul. 13, 2005, 1 page.

Boston Medical, http://www.bosmedtech.com/, retrieved Oct. 10, 2001, 2 pages.

Kivalo: Wireless Healthcare Informatics, http://www.kivalo.com/, retrieved Oct. 10, 2001, 2 pages.

"Digital Angel: Making Your World a Little Safer . . . ," http://digitalangel.net/da/, retrieved Oct. 10, 2001, 3 pages.

Cadionet, http://www.cardionet.com/, retrieved Oct. 10, 2001, 1 page.

The HomMed Central Station, http://www.hommed.com/patients_families/central_station.asp, retrieved Oct. 10, 2001, 1 page.

"BodyMedia Introduces Sense Wear Pro Armband Wireless Body Monitoring Device," http://www.thinkmobile.com/news/00/39/23/, retrieved Oct. 10, 2001, 3 pages.

"Micropaq," Welch Allyn, http://www.monitoring.welchallyn.com/products/wireless/micropaq.asp, retrieved Apr. 16, 2003, 2 pages.

Ideal Life BP-Manager, Model BPM 0001; Ideal Life Pod, Model ILP 0001, Ideal Life Inc., K060504, Mar. 14, 2006, 7 pgs.

Ideal Life Pod (Model ILP 0001), Ideal Life Ince., K080535, Jul. 3, 2008, 16 pgs.

OMRON Automatic Blood Pressure Monitor With Intellisense, Models HEM-773, HEM-773AC, OMRON Healthcare. Inc., K021682, 4 pgs.

Carematix Wellness System, Carematix Inc., K031840, Oct. 10, 2003, 6 pgs.

In Touch Diabetes Management Software, Lifescan, Inc., Apr. 29, 1999, 6 pgs.

OMRON Instruction Manual, Intellisense Automatic Blood Pressure Monitor with Easy Wrap Cuff, Model HEM-77AC, © 2003, 20 pgs.

Our Solutions, Carematix Wellness System, © 2002, 1 pg.

Update to IN TOUCH ® Diabetes Management Software, Lifescan, © 2001, 1 pg.

\* cited by examiner

MEDICAL MONITORING/CONSUMABLES TRACKING DEVICE

This application claims the priority of application Ser. No. 60/487,471, entitled Medical Monitoring/Consumables Tracking Device, which was filed on Jul. 15, 2003, and is a continuation of application Ser. No. 10/963,205 (now U.S. Pat. No. 8,034,294), entitled Medical Monitoring/Consumables Tracking Device, which was filed on Oct. 11, 2004 and is a continuation of application Ser. No. 10/892,320, entitled Medical Monitoring/Consumables Tracking Device, which was filed on Jul. 15, 2004, the disclosures of all of which are incorporated herein by reference in their entireties.

BACKGROUND OF THE INVENTION

The present invention relates to portable medical monitoring devices, and more particularly, medical devices that use consumables in connection with testing or determining a physiological parameter of a subject. This application incorporates by reference the entire disclosures of application Ser. No. 09/975,097 (United States Patent Pub. No. 2003/0073884), titled MEDICAL MONITORING DEVICE AND SYSTEM, filed Oct. 11, 2001, application Ser. No. 60/562,877, titled MEDICAL MONITORING SYSTEM, filed Apr. 16, 2004, and application Ser. No. 60/493, 904, titled PERSONAL HEALTH MANAGEMENT DEVICE, METHOD AND SYSTEM, filed Jul. 7, 2003.

Many diabetics use glucose monitoring devices to assist in controlling their condition. Glucose monitoring devices typically use glucose monitoring strips, on which a blood sample is placed, for testing the subject's blood glucose level. Self-monitoring is essential for controlling diabetes and preventing complications, such as cardiovascular disease, stroke, eye disease, foot problems that may lead to amputation, etc. The level of self-monitoring recommended varies between patients and the type of diabetes, which may be from once a day for type II diabetes to three times a day for type I diabetes. Accordingly, diabetics are periodically provided with test strips in quantities 30, 90, 120, etc., which are typically covered by health insurance, Medicare, Medicaid, etc. Many diabetics, however, do not require as many test strips as provided and many simply do not follow the recommended level of self-monitoring, which in both instances results in an excess and correspondingly inefficient allocation of allocation of test strips. The inefficiency is compounded over the estimated millions of diabetics that use glucose monitoring devices.

SUMMARY OF THE INVENTION

In one aspect of the present invention, a medical monitoring device and method are provided for testing or determining at least one physiological parameter of a subject using a consumable, and to track or otherwise monitor use of a consumable, e.g., a consumable used to conduct a test or to be consumed or otherwise used by a subject, e.g., a subject associated with or using a medical monitoring device. In one embodiment, the medical monitoring device is capable of storing, transmitting and/or displaying data, including glucose level, consumable usage, etc. According to one aspect of the invention, medical monitoring devices, systems, and methods are provided for tracking consumables used in connection with medical monitoring devices over a given period of time and making determinations relating to usage, resupply, record keeping, payment, etc.

In one embodiment, the medical device includes an electronic controller, one or more sensors, and an electronic memory device for at least temporarily storing sensor data and/or other data. Preferably, the device includes a display. In one embodiment, the device includes a communication unit for communication with an external device such as a local or a remote computer, e.g., wirelessly, wire, or a combination thereof. Such communication may, e.g., be through a base or local unit which, e.g., services one or more associated medical devices, e.g., by relationship, e.g., a family, household, medical group, etc. relationship, or by location, etc.

In another embodiment, the device includes means for communicating data over a communication network, by wire or wirelessly, to a remote computer or database which, e.g., stores, processes, etc. the data for access and/or use by various parties such as the subject, the subject's care provider(s), insurance companies, suppliers, etc., and other parties, or to such authorized parties. An information provider or other party may provide or otherwise operate the remote computer or database and provide access, etc., to stored information to such parties according to any suitable business model.

The communications means may be internal modem, wireless transmitter/receiver combination, etc. Alternatively, or in addition, the medical monitoring device may interface with suitable communicatively enabled devices for communicating data to the authorized parties. In addition, the monitoring device may be adapted to compute strip usage, provide strip usage to a remote computer, and receive strip usage data stored in or computed by a remote computer.

In another aspect, a method of tracking consumable usage in connection with a medical monitoring device is provided that comprises determining at least one physiological parameter of a subject, determining consumable usage data associated with the at least one parameter for at least one subject, and communicating at least the usage data to a remote computer. Embodiments of the invention may use the data in connection with, e.g., determining consumable(s) usage, determining consumable(s) resupply parameters, subject compliance, insurance company requirements and payments, record keeping, e.g., on a subject, insurance company, insurance company payment, record keeping on a subject, insurance company, peer group, demographic, etc. basis or other basis, statistical analysis, etc. Information related to the above may be communicated to the medical monitoring device or to authorized parties.

In another embodiment, at least one alert message is communicated to either the subject or an authorized party or parties in connection with consumable usage, e.g., when consumable usage is different from a given value or is not within a given range, or the rate of consumable usage is different from a given value or not within a given range. In one embodiment, the alert message alerts that additional supplies of a consumable, e.g., strips are or will be needed.

In another aspect of the invention, a medical monitoring device is provided that includes at least one sensor for detecting actual usage of at least one consumable, and an electronic controller and an electronic memory device or buffer which provide for storage, at least temporarily, of information provided by the at least one sensor. In one embodiment, the medical monitoring device includes at least one sensor for determining one or more physiological parameters of a subject and a display device for displaying the physiological parameter. The sensor may determine the physiological parameter with the aid of a consumable. The physiological parameter data may also be stored on the electronic memory.

In one embodiment, the medical monitoring device includes a blood glucose sensor that produces a signal or signals for use in determining blood glucose level using a consumable and a display device for displaying blood glucose level. In this instance, the signal(s) produced by the blood glucose sensor are used to detect, log or register use of the consumable. The device may include a sensor for monitoring other physiological parameters, such as pH, Ketone, cholesterol, triglyceride, electrolyte level, blood oxygen level, heart rate, and blood pressure.

In one embodiment, the medical monitoring device includes a communications unit for communicating stored data, such consumable data, e.g., usage, and physiological parameter data, over a communication network to a remote computer. The device may further include a data logger for tracking a number of consumables used and software and or logic for tracking consumable usage over time, e.g., to compute a rate of consumable usage based on consumable usage data.

In another aspect of the invention, a medical monitoring device is provided that includes at least one sensor, such s a blood glucose sensor for determining at least one physiological parameter of a subject using at least one consumable, an electronic controller electrically and a memory device which cooperate to store at least temporarily consumables usage data related to the at least one's sensor's detection of actual consumable usage and physiological parameter data, and a display device for displaying at least one of consumable usage data and physiological parameter data thereon.

In another aspect of the invention, a medical monitoring system is provided that includes at least one computer communicatively connected to at least one monitoring device over a communication network. The monitoring device is generally capable of detecting actual usage of at least one consumable for a subject and communicating usage data to the remote computer. In one embodiment, the computer is capable of processing usage data and determining a future allocation of consumable for the subject, such as based on usage data, statistical analysis of the usage data, a previous allocation for the subject, or a combination thereof. The computer may reduce the number of consumables allocated to the subject to reflect consumable usage below at least one of an initial allocation and a previous allocation. The computer may also determine whether consumable usage falls outside a value range and communicate a message to the subject or an authorized party indicating that consumable usage has fallen outside of the value range.

In another aspect of the invention, a medical monitoring system is provided that includes at least one computer communicatively connected to at least one monitoring device over a communication network. The monitoring device includes at least one sensor, such as a blood glucose sensor, for determining one or more physiological parameter of a subject using at least one consumable and detecting actual usage of the consumable therewith. In this instance, the monitoring device is generally capable of communicating usage data and/or physiological parameter data to the remote computer.

BRIEF DESCRIPTION OF THE DRAWINGS

The invention is illustrated in the figures of the accompanying drawings which are meant to be exemplary and not limiting, in which like references are intended to refer to like or corresponding parts, and in which.

DETAILED DESCRIPTION OF THE PREFERRED EMBODIMENT

The term consumables is used herein to generally denote items used in connection with medical monitoring that have a limited life or limited number of uses, such as glucose test strips, that because of which must be replenished periodically. Consumables can include medicines as long as the monitoring device can track consumption of the medicine. Although the present invention may be described by way of example in relation to glucose monitoring and glucose monitoring consumables, it is understood that the present invention is equally applicable to monitoring many other physiological parameters and with other types of consumables, such as lances, needles, thermometer covers, etc., and is thus not limited thereto.

Figure 1:
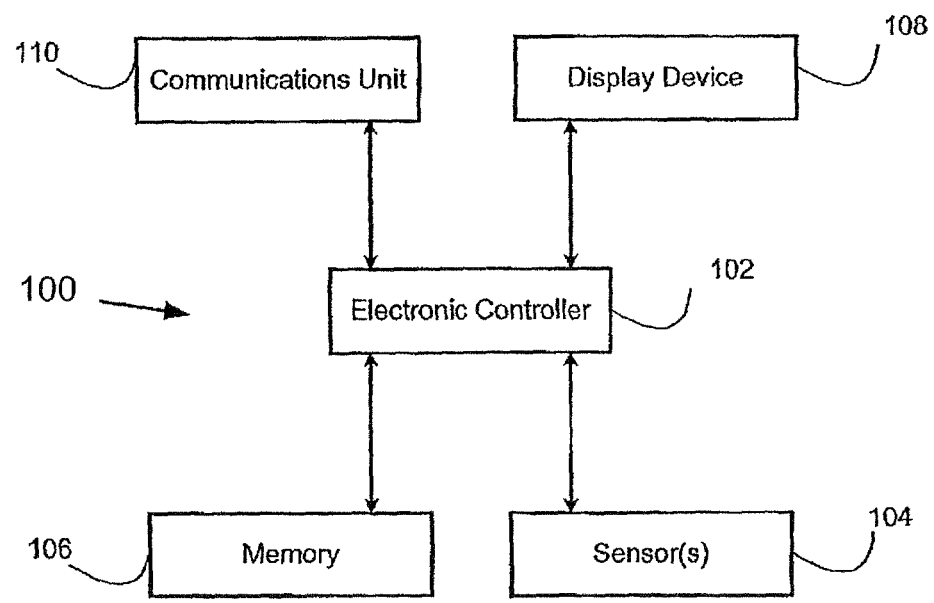
FIG. 1 is a block diagram of a medical monitoring device according to one embodiment of the invention.

Referring to FIG. 1, in one aspect of the present invention, a medical monitoring device 100 is provided, which includes an electronic controller 102, a display device 108, an electronic memory 106, and one or more sensors 104 for detecting consumable usage and/or testing or otherwise determining at least one physiological parameter of a subject using the consumable. The present invention, beneficially allows an authorized party to determine compliance based on actual usage of the consumable as opposed to indirect or assumed usage based on reporting acts from a subject. For example, actual usage may be assured with a device adapted to determine both usage and blood glucose from a blood glucose sensor.

It is understood that the device 100 may detect consumable usage in a number of ways. For example, with respect to glucose monitoring, the device 100 may sense that a strip has been used every time a user attempts to take a glucose reading with a strip. In this instance, the sensor 104 detects actual strip usage and sends a signal to the controller 102 indicating that consumable usage has been detected. Similarly, with respect to medications, the device 100 may include a receptacle for the medication and a pill counting mechanism that counts pills or a mechanism that determines usage based on weight or any other method for gauging the level of a medication, e.g., in liquid form, in the receptacle. Actual usage with respect to medications may be determined based on corroboration with regard to a subject's expected reaction to the medication, such as increased blood pressure, heart rate, effects of the medication, etc. Similarly, with time-release medication, actual usage may be determined based on corroboration between the time the medicine was taken or removed from the bottle and the expected effects of the medication. Actual usage with medications may also be determined by including a micro-transmitter in the medicine, e.g., a pill, which sends a signal to the medical monitoring device when the pill comes into contact with digestive fluids indicating actual consumption. The present invention beneficially allows a user or another interested party to track data with regard to consumables actually used by the subject for a given period of time.

The device 100 may further include a data logger or a counter, or any other means for tracking the number of consumables used, and may include a clock means, which may be embodied software, hardware, or a combination thereof, for tracking consumable usage over a period of time. It is understood that the logger or counter may be embodied in electronic hardware, software, or a combination thereof. In this respect, in one embodiment, the medical monitoring device 100 is capable of storing and/or displaying consumable usage data and/or physiological data, such as glucose level, heart rate, blood pressure, etc., or a combination thereof. Consumable usage data may be stored in a variety of forms, such as in the form of a table that includes a list of date stamps indicating that a consumable was used and when the consumable was used, a count or the number of units used from a particular reference date, the rate that units are used, e.g., units/month, over any given period of time, etc. The medical monitoring device 100 may be configured in a variety of shapes and sizes. In one embodiment, the monitoring device is portable in size so that the subject may carry around the device with relative ease.

It is understood that various types of blood glucose sensors may be incorporated into the present device. In one embodiment, the monitoring device 100 includes a blood glucose sensor for determining blood glucose level with consumables, such as glucose test strips, pads, cards, etc. Blood glucose sensors generally produce a signal that is used to determine the rate that blood is absorbed into respective consumables or test strips, which is translated into a glucose blood level that may be stored, e.g., in the electronic memory 106 along with the consumable usage data. The medical device 100 may also include sensors 104 capable of monitoring other physiological parameters other than or in addition to the subject's blood glucose, such as pH, Ketone, cholesterol, triglyceride, electrolyte levels, or blood oxygen level, which may also be stored along with usage data.

In one embodiment, the device also includes a communications unit 110 or other means for communicating the stored data over a communication network, by wire or wirelessly, to authorized parties, such as the subject's physician, an insurer, the pharmacy, etc., or an information provider that stores the information and provides access to the information for such parties. A communication network includes a public or private switched telephone network, the Internet, private or public networks, wireless networks, or any other suitable communication network.

Figure 2:
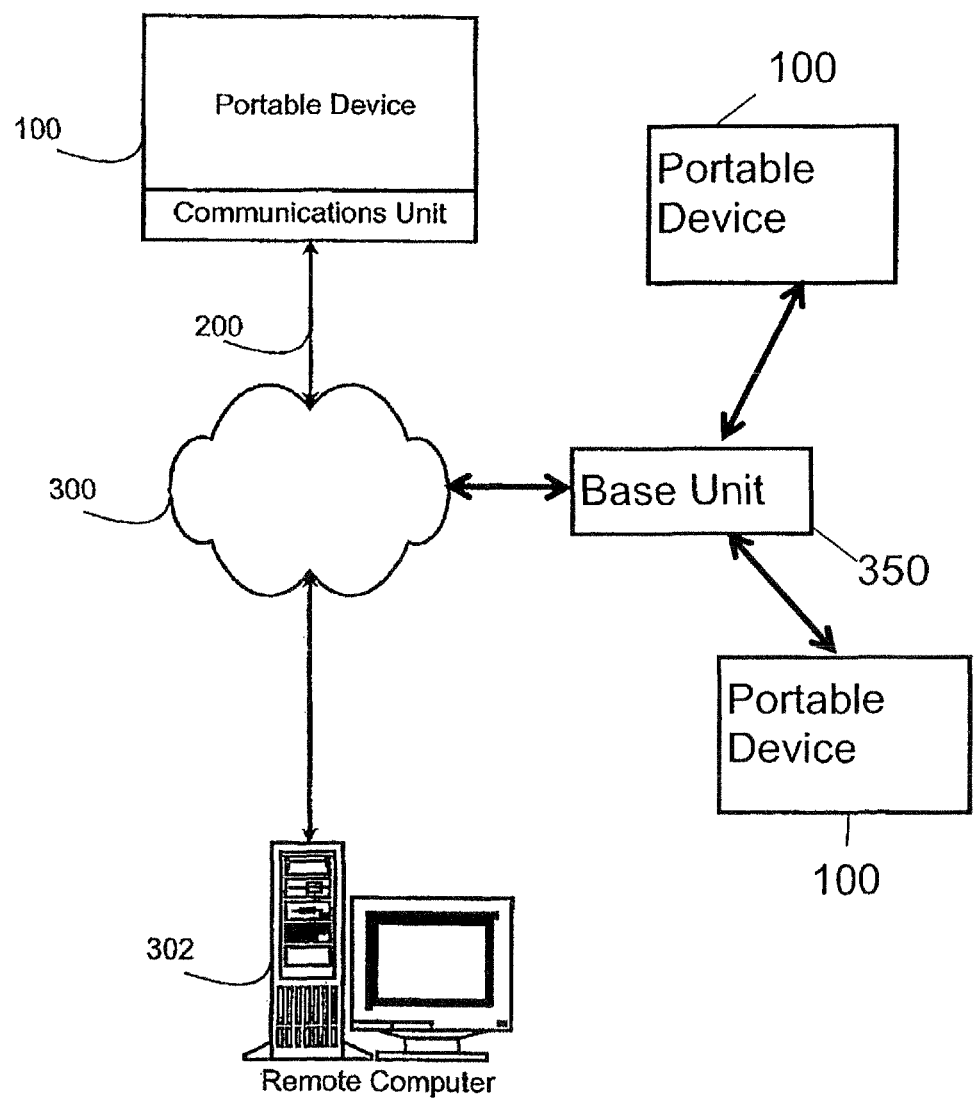
FIG. 2 is a block diagram of a medical monitoring system according to one embodiment of the invention, FIG. 3 are flow diagrams of a medical monitoring methods each according to one embodiment of the invention.

Referring to FIG. 2, the communications unit 110 may be incorporated into the device 100, such as an internal modem, wireless transmitter/receiver combination, etc. Alternatively, or in addition, the medical monitoring device 100 may interface with suitable communicatively enabled devices, such as personal computers, special purpose computers, two-way pagers, two-way radios, telephones, cell phones, etc., e.g., with a docking station, for communicating data to the respective authorized party. Communication may also be through a base or local unit 350 which, e.g., services one or more associated medical devices 100, e.g., by relationship, e.g., a family, household, medical group, etc. relationship, or by location, etc. The base station beneficially allows a plurality of devices to interface with a single communicatively enabled device for communicating data to the remote computer, which is particularly useful in instances where a plurality of devices 100 are used in a single location, such as a hospital, a household, etc., with a limited amount of communicatively enabled devices. In this instance, the controller 102 generally controls data communication between the respective components of the monitoring device 100, and between the monitoring device 100 and at least one remote computer or device 302 connected to the device 100 either directly or over a communications network 300.

Figure 3:
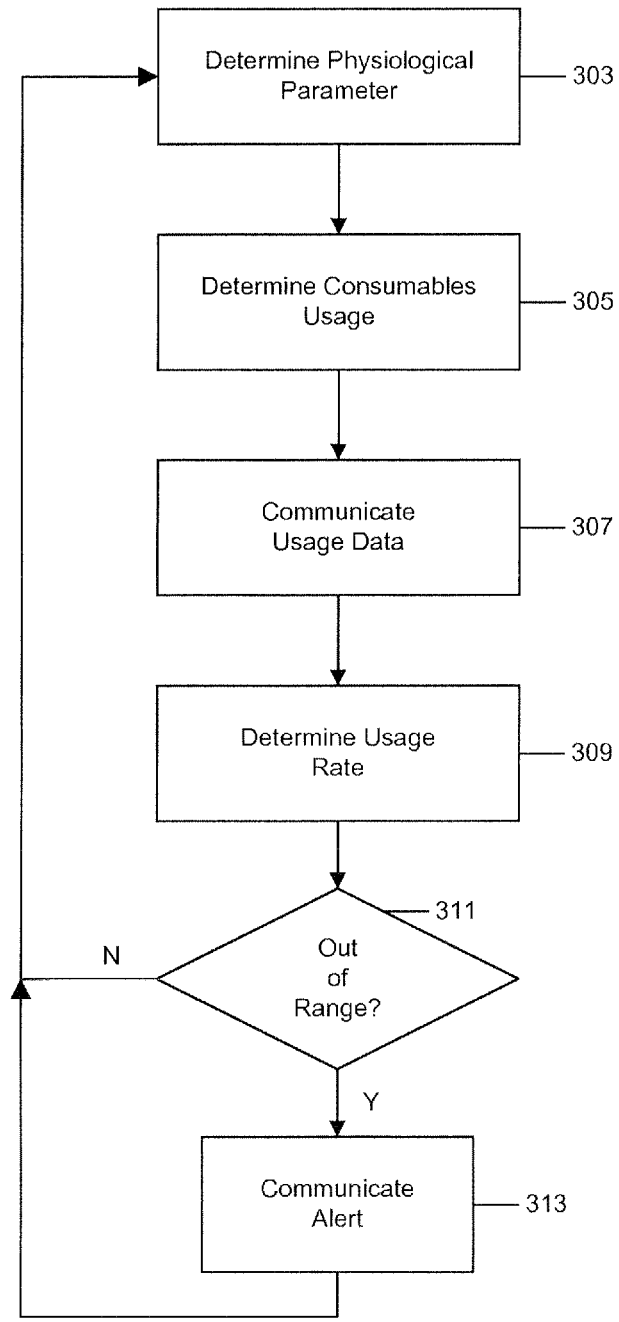

Referring to FIG. 3a, in another aspect, a method of tracking consumable usage in connection with a medical monitoring device is provided that includes one or more of the following steps: determining at least one physiological parameter 303, determining consumable usage data for at least one subject 305, and communicating at least the usage data 307 to a remote computer 302, such as a server computer, where the information may be stored for use with regard to, e.g., allocating consumables, compliance determinations, statistical analysis, etc., determining a usage rate 309, and communicating an alert to the subject or another authorized party 313 if at 311 the usage rate falls outside of a predefined range. Consumable usage data may also be used for ordering consumables, e.g., when it is determined that the subject may have a low supply of consumables based on the rate that consumables are used, and arranging payment for consumables once the consumables have been ordered and/or shipped to the subject. In this instance, the computer 302 sends an order to replenish the subject's supply to a consumables supply house, such as a pharmacy.

In another aspect, of the invention, a method of tracking consumable usage in connection with a medical monitoring device is provided that comprises determining at least one physiological parameter of a subject 303, determining consumable usage data associated with the at least one parameter for at least one subject 305, and communicating at least the usage data to a remote computer or a database 307 which, e.g., stores, processes, etc., the data for access and/or use by various parties, such as the subject, the subject's care provider(s), insurance companies, suppliers, etc., and other parties, such as the subject's physician, an insurer, the pharmacy, etc. The usage data may then be used for determining one or more of the following supply variables: consumable(s) usage, determining consumable(s) resupply parameters, subject compliance, insurance company requirements and payments, record keeping, e.g., on a subject, insurance company, insurance company payment, record keeping on a subject, insurance company, peer group, demographic, etc., basis or other basis, statistical analysis, etc.

The remote computer 302 may further communicate information, such as consumable allocation, statistical data regarding consumables allocation and actual usage, physiological parameters, etc, compliance reminders, etc., to the portable device 100 or to authorized parties. Communication may be initiated by a user or automatically, e.g., with programming that initiates communication at predetermined time intervals, such as twice a day, daily, weekly, monthly, etc.

In one embodiment, a remote computer 302, such as a web server, processes consumable usage data, such as the number of glucose strips used, the rate strips were used for a given period of time or from a reference time, such as the time of a previous communication, for analysis with regard to, e.g., allocation, compliance, and/or statistical analysis. In some embodiments, a value range may be associated with the rate of consumable usage, such as the rate of strip or medication usage, which may be compared with measured usage to determine if an automatic message alert should be transmitted. The particular value range used for generating message alerts may be ascertained based on a parameter associated with consumables usage for a particular monitored person. For example, a value range of between 20 to 40 strips per week may be used as a basis for alerts for a particular user with a strip allocation of 120 strips per month, in which instance strip usage of less than 20 may trigger an alert, e.g., to the subject user or an authorized party, indicating insufficient usage. Usage of over 40 may similarly trigger an alert indicating over usage based on the allocated quantities.

In one embodiment, the remote computer 302 uses consumable usage data with or without specific physiological characteristic to calculate statistical data, such as consumable usage rate over time intervals, such as daily, weekly, monthly intervals, etc, for the previous month, previous two months, etc, and/or to calculate a variance, standard deviation, least square, or a distribution, which may also be used to trigger automatic messaging regarding consumable usage.

In another embodiment, the remote computer 302 determines a future allocation of consumables for the user based on the usage data, statistical analysis of the usage data, and/or based on previous allocations of consumables to the subject. For example, assuming a type I diabetes subject is allocated 90 glucose test strips for a first month and the device 100 and/or the remote computer 302 determine that the subject used 50 test strips, the excess 40 test strips from the initial or previous allocation may be reflected in the subsequent allocation, for instance, to reduce the amount of the allocation for the next month to 50 test strips. In this example, the subject should be able to maintain a 90-test strip supply for the month. Moreover, the overall supply for a given period may be reduced to reflect repeated usage below the initial or a previous allocation level. For instance, assuming in addition to the above example an average usage of 50 test strips per month, the allocation may be reduced so that the subject maintains a 50-test strip supply for the month. An appropriate safety factor may be included in the allocation to limit the risk of the subject running out of test strips.

In one embodiment, the monitoring device 100 or the remote computer 302, such as a server, includes automatic message alert functionality alerting the monitored person and/or authorized parties when consumable usage is more than, less than, or equal to or is outside of a given range. The authorized parties may monitor with a communicatively enabled devices, such as a pager, telephone, mobile telephone, PC, laptop computer, or PDA. In one embodiment, the monitoring device 100 is capable of receiving and displaying messages from the authorized parties. The alerts may be used for instance to trigger compliance with, to initiate allocation for replenishing the subject's supply of consumables, to inform the subject of a change in allocation, etc. Additionally, an alert may be provided if it is determined that at least one physiological parameter is out of range, e.g., high or low glucose level.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application. It is intended that the scope of the invention be defined by the claims appended and their equivalents.

What is claimed is:

1. A medical monitoring device comprising:
   a sensor which is configured to provide physiological parameter signals which relate to at least one physiological parameter of a subject being monitored and a medication usage determining mechanism which is configured to provide usage signals related to consumption of at least one consumable to be taken and consumed by the monitored subject and which consumption the physiological parameter signals provided by the sensor can indicate; and
   an electronic controller and at least one a memory device, the controller being programmed to provide to the at least one memory device for storage therein at least temporarily physiological parameter data relating to the at least one physiological parameter based on the physiological parameter signals provided by the sensor, and usage data related to consumption of the at least one consumable, wherein the usage data is based on (a) the usage signals provided by the determining mechanism and (b) the physiological parameter signals provided by the sensor.

2. The medical monitoring device of claim 1, wherein the consumable comprises a medication.

3. The medical monitoring device of claim 1, comprising a display device which is configured to display data stored in the memory device provided by the at least one controller related to at least one of the at least one physiological parameter and usage data.

4. The medical monitoring device of claim 1, wherein the sensor is configured to provide physiological parameter signals related to at least one of: blood pressure, pH, Ketone, cholesterol, triglyceride, electrolyte level and blood oxygen level.

5. The medical monitoring device of claim 1, comprising a communications unit which is configured to communicate data stored in the at least one memory device for receipt over a network by at least one computer.

6. The medical monitoring device of claim 1, wherein the controller is programmed to compute a rate of consumable usage based at least on usage data stored in the at least one memory device and time.

* * * * *